United States Patent [19]

Pierce et al.

[11] Patent Number: 4,560,551
[45] Date of Patent: Dec. 24, 1985

[54] BEETLE ATTRACTANT

[76] Inventors: Aldona M. Pierce; Harold D. Pierce, both of #6 - 7088 Inlet Dr., Burnaby, B.C., Canada

[21] Appl. No.: 500,083

[22] Filed: Jun. 1, 1983

[51] Int. Cl.$^4$ ............................................ A01N 25/00
[52] U.S. Cl. ...................................................... 424/84
[58] Field of Search ......................................... 424/84

[56] References Cited

U.S. PATENT DOCUMENTS

| | | | |
|---|---|---|---|
| 1,540,649 | 6/1925 | Power et al. | 424/84 |
| 2,257,711 | 9/1941 | Colbeth | 424/84 |
| 3,225,102 | 12/1965 | Thompson | 424/84 |
| 4,404,185 | 9/1983 | Maccone et al. | 424/84 |

FOREIGN PATENT DOCUMENTS

| | | | |
|---|---|---|---|
| 0066113 | 12/1982 | European Pat. Off. | 424/84 |
| 0118524 | 10/1978 | Japan | 424/84 |

OTHER PUBLICATIONS

A. F. Kydonieus & N. Beroza (eds.), "Insect Suppression with Controlled Release Pheromone Systems", vol. I, II, CRC Press, Title pages only.
"Zoecon Insect Monitoring Systems", brochure by Zoecon Corp., Palo Alto, CA; copyright notice 1981.
D. K. Mueller, "Pheromones", Pest Control, Feb. 1982, pp. 22-24.
D. K. Mueller, "Pheromones—Part 2", Pest Control, Mar. 1982, pp. 26-28.
S. R. Loschiavo et al., "An Improved Trap to Detect Beetles (Coleoptera) in Stored Grain", The Canadian Entomologist, Mar. 1973, in part. p. 438.
H. Z. Levinson et al., "Trapping of Storage Insects by Sex and Food Attractants as a Tool of Integrated Control", Chemical Ecology: Odor Communication in Animals, 1979, in part. p. 330.
Loschiavo et al., "A Survey of Stored Product Insects in Hawaii", Proceedings, Hawaiian Entomological Society, vol. XIII, No. 1, Apr. 1979, in part. see Fig. 8 F, G, p. 118.
D. B. Pinniger, "The Use of Bait Traps for Assessment of Stored-Product Insect Populations", U.S.D.A. Cooperative Economic Insect Report 25: pp. 907-909, (1975).
Reuter Buyers Catalogue, undated.
Buttery et al., "Volatile Companents of Alfalfa: Possible Insect Host Plant Attractants", J. Agric. Food Chem., vol. 28, No. 5, (1980), pp. 978-981.
Buttery et al., "Components of Almond Hulls: Possible Navel Orangeworm Attractants and Growth Inhibitors", J. Agric. Food Chem., vol. 28, No. 2, (1980).
Buttery et al., "Oat Leaf Volatiles: Possible Insect Attractants", J. Agric. Food Chem., vol. 30, 791-792, (1982) abs.
Olfactory Response to Beetle-Produced Volatiles and Host-Food Attractants by Oryzaephilus surinamenis and O. mercator, Canadian Journal of Zoology, vol. 59, No. 10, 1981, pp. 1980-1990.
Chem. Abs. 97: 36057r, Buttery et al., 1982.
Pierce et al., Canadian Journal of Zoology, vol. 59, 10, 1981, pp. 1980-1990.

Primary Examiner—Albert T. Meyers
Assistant Examiner—John M. Kilcoyne

[57] ABSTRACT

An insect trap is provided which contains an attractant comprising a sufficient amount of unsaturated oxacyclododecanone selected from the group consisting of (Z-12-methyloxacyclododec-4-en-2-one (I),(Z,Z)-12-methyloxacyclododeca-4,7-dien-2-one (II), and the alkyl substituted products of the foregoing, the amount of the attractant being sufficient so as to effectively attract O. mercator beetles. The attractant may also comprise an aldehyde, preferably hexanal, octanal, or nonanal, and preferably in combination with I or II, or both.

3 Claims, 9 Drawing Figures

Fig. 1.

O. MERCATOR
GAS CHROMATOGRAM OF PORAPAK Q-TRAPPED BEETLE VOLATILES

Fig. 2.

RESPONSE BY O. MERCATOR (♂+♀) IN TWO-CHOICE BIOASSAY

BEETLE ATTRACTANT

FIELD OF THE INVENTION

This invention relates to a trap containing a beetle attractant, in particular an attractant for *Oryzaephilus mercator* beetles, more particularly known as the merchant grain beetle.

DESCRIPTION OF PRIOR ART

*O. mercator* is a well established household pest in North America and is associated with processed cereal products, particularly those of high oil content disposed in heated premises. In addition, *O. mercator* can also infest stored grain products. Early detection of the insects in commercial facilities is of utmost importance in preventing large losses, since under favourable conditions insects grow and multiply rapidly. It has been disclosed in the paper by A. M. Pierce et al in *Canadian Journal of Zoology*, Vol. 59, 10, 1981, pp. 1980–1990, that a crude extract of volatiles from *O. mercator* beetles or beetle frass can be obtained which appears to exhibit an effect in attracting the beetles. However, such extracts contain a great number of compounds, many of which by themselves are present in insufficient concentrations to effectively attract *O. mercator* beetles. In particular, the unsaturated oxacyclododecanones disclosed in this application, were present in the bioassays described in that paper in either zero amounts, or in amounts which by themselves were insufficient to effectively attract beetles. In addition, the aldehydes disclosed below were present only in very low amounts which by themselves were insufficient to effectively attract beetles.

FIELD OF THE INVENTION

This invention relates to an insect trap which contains an attractant preferably comprising a sufficient amount of an unsaturated oxacyclododecanone. The unsaturated oxacyclododecanone is selected from the group consisting of (Z)-12-methyloxacyclododec-4-en-2-one and (Z,Z)-12-methyloxacyclododeca-4,7-dien-2-one. A sufficient amount of the unsaturated oxacyclododecanone is provided in the trap so as to attract *O. mercator* beetles.

Preferably, the amount of unsaturated oxacyclododecanone is such that it is primarily responsible for attraction of the beetles to the trap (that is, responsible for the majority of the attraction of the beetles).

The attractant in the trap additionally usefully comprises a non-aromatic aldehyde which preferably has only one carbonyl group and from 6 to 9 carbon atoms. Most preferably the aldehyde is a normal alkyl aldehyde, which is usefully either hexanal, octanal, or nonanal. Particularly useful is the combination of (Z)-12-methyloxacyclododec-4-en-2-one and n-nonanal. Preferably at least about 10 ug of the unsaturated oxacyclododecanone is present in any of the foregoing traps.

The unsaturated oxacyclododecanone utilized in the trap, may conveniently comprise a mixture of the two enantiomers of it. Preferably though, the (R)-enantiomer is utilized in the case of either unsaturated oxacyclododecanone.

An insect trap which contains at least about 1 ug, and preferably 10 ug of an aldehyde as previously described, is also disclosed in the present application. In addition, a method of trapping *O. mercator* beetles is also disclosed which utilizes any of the traps previously described.

DRAWINGS

Embodiments of the invention will now be described in detail, with reference to the drawings in which.

DETAILED DESCRIPTION OF THE INVENTION

It has been discovered that hexanal, octanal, and nonanal as well as (Z)-12-methyloxacyclododec-4-en-2-one (I) and (Z,Z)-12-methyloxacyclododeca-4,7-dien-2-one (II) are effective attractants for *O. mercator* (i.e. merchant grain beetles). The structures for I and II are as follows:

The foregoing names of I and II are based upon the *Chemical Abstracts* system of nomenclature, and can also be named (Z)-3-dodecen-11-olide or (Z,Z)-dodeca-3,6-dien-11-olide respectively. In addition, it has also been discovered that a greater attraction of the *O. mercator* beetles is obtained when I or II are utilized in combination with one or more of the aldehydes described, and that the R-(−) enantiomer of I was a more effective attractant for the beetles than the S-(+) enantiomer of I. The isolation of I and II, as well as their chemical synthesis and bioassays performed utilizing I and II and the aldehydes, are described below.

Isolation of I and II

Air was drawn at approximately 1.9 L/min with a water aspirator successively through water (to prevent dessication of beetles), a charcoal-filled (50–80 mesh) air scrubber (2.4 cm OD×12 cm), a two-piece cylindrical chamber (15.5 cm ID×27 cm) and, finally, a glass trap filled with PORAPAK Q[1] (2.4 cm OD×20 cm). Approximately 100,000 adult *Oryzaephilus mercator* beetles of mixed sex and 1.5 kg of rolled oats were placed in the large chamber. After 21 days of aeration, the PORAPAK Q[1] trap was removed.

Figure 1:
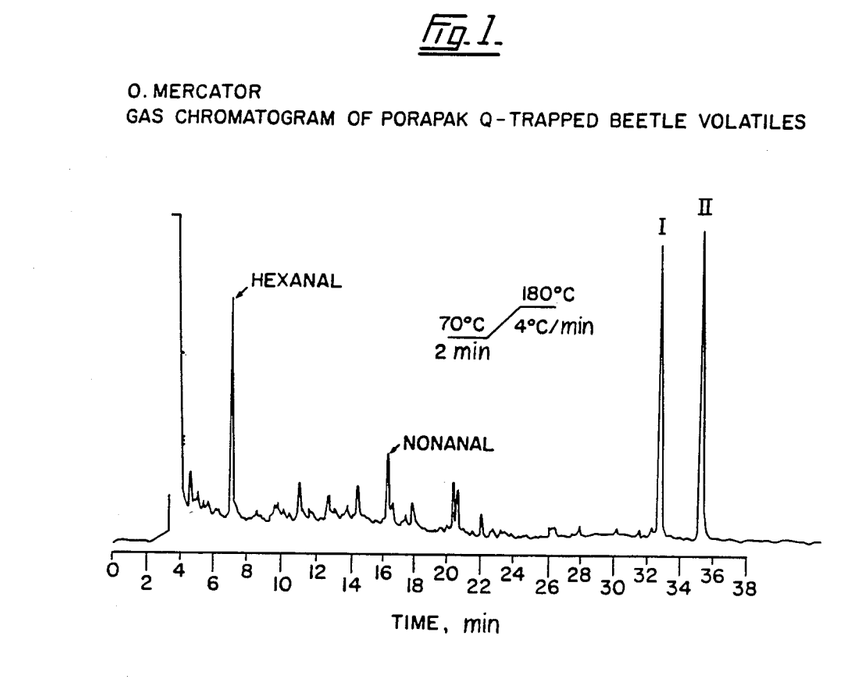
FIG. 1 is a gas chromatogram of *O. mercator* beetle volatiles trapped in a manner to be described.

Volatiles were recovered by extracting the PORAPAK Q in a Soxhlet extractor with purified pentane for at least 24 hr. The extract was concentrated to about 5 mL by distilling the pentane through a 30 cm Dufton column. The volatiles were analyzed by gas-liquid phase chromatography (glpc) on 48 m×0.5 mm ID open-tubular glass column coated with SUPEROX-4[2]. Helium was the carrier gas, and the temperature program was as follows: 70° C. for 2 min, then 4° C./min to 180° C. (hold). The gas chromatogram of the volatiles is shown in FIG. 1. Compounds I and II were individually isolated by isothermal (170° C.) micropreparative glpc on a 10 ft×⅛ in ID stainless steel column packed with 10% SP-1000[3] on SUPELCOPORT[4] (100/120 mesh). Analysis of the isolated compounds I and II on the aforementioned open-tubular glass column (see above) revealed that the compounds were better than 99% pure. Approximately 1 mg of each was produced per month of aeration.

1. PORAPAK Q is a trademark of Waters Associates Inc., Milford, Mass., for a copolymer of ethyl vinylbenzene and divinylbenzene.
2. SUPEROX-4 is a trademark of RSL, Eke, Belgium, for a polyethylene glycol-type liquid phase for gas chromatography.
3. SP-1000 is a trademark of Supelco Inc., Belleforte, Penn., for a polyethylene glycol-type liquid phase for gas chromotography.
4. SUPELCOPORT is a trademark of Supelco Inc., Belleforte, Penn., for a diatomaceous-type solid support for gas liquid chromatography.

The collecting of volatiles from beetles being fed on oats produces relatively large amounts of I and II as well as hexanal, octanal and nonanal, at least in comparison to the disclosure in the Pierce et al paper, where the volatiles were extracted from beetles by themselves. A calculation of the amounts of I which may be present in the bioassays of the Pierce et al paper, indicates that under the experimental procedure utilized therein, approximately 100,000 beetle hours equals about 1 ng of I. As a result, the maximum amount of I in the bioassays of FIG. 5 of the Pierce et al paper, would be about 1.75 ng. Further, similar calculations show that in the trap used to generate the results shown in FIG. 5 of that paper there could have been maximum amounts of about 20 ng of hexanal, 20 ng of nonanal, and about 3 ng of octanal, and negligible amounts of II. Thus, as will be seen from the data given below, the maximum amount of I present in the foregoing, would not be sufficient so as to effectively attract beetles, that is produce a response of substantially more than about 60% (bearing in mind that a 50% response means an equal number of beetles are attracted to the control in the 2-choice bioassay) and attract beetles from a practically useful range over a practically useful period of time.

SCHEME II

-continued
SCHEME II

II

Chemical Synthesis of (R,S)-(±)-II

The chemical synthesis of II to be described produces a racemic mixture of the enantiomers. The synthesis of II commenced with 5-hexyn-1-ol (2) and 3-butyn-1-ol (3), and was performed as shown in Scheme II supra. 5-Hexyn-1-ol (2) was oxidized with pyridinium dichromate in methylene chloride to the aldehyde 4. Reaction of 4 with methyl magnesium bromide gave the alcohol 5, which was protected as the tetrahydropyranyl ether, giving 6 in good yield as one segment of the carbon skeleton of II. For the other segment, 3-butyn-1-ol (3) was protected as the tetrahydropyranyl ether 7, and chain-extended by one carbon by reaction of the lithium salt of 7 with paraformaldehyde, giving the propargyl alcohol 8. Tosylation of 8 gave the second required fragment, 9.

Coupling of 6 and 9 was affected by cuprous bromide-catalyzed reaction of the Grignard of 6 with 9, yielding the 3,6-diyne 10. Crude 10 was deprotected with p-toluenesulfonic acid in dry methanol to give diol 11, which was oxidized with Jones reagent by the inverse addition[5] method to the keto-acid 12. Selective reduction of the ketone with sodium borohydride yielded the hydroxy-acid 13. Subsequent stereoselective reduction of the diyne 13 with P-2 Nickel[6] gave the Z,Z-3,6-dienoic acid 14. Finally, cyclization of 14 with 2-chloro-N-methyl-pyridinium iodide[7] in acetonitrile gave II, spectroscopically and chromatographically identical to the naturally-produced material. Due to the instability of intermediates 10 through 14, it is essential to conduct the last five reactions as quickly as possible, and with the minimum number of purification steps.

5. B. C. Holland and N. W. Gilman, *Syn. Comm.*, 4, 203 (1974).
6. C. A. Brown and V. K. Ahuja, *J. Chem. Soc. Chem. Commun.*, 553 (1973).
7. T. Makaiyama, K. Narasaka and K. Kikuchi, *Chem. Lett.* 441 (1977).

Preparation of 5-hexyn-1-al (4)

5-Hexyn-1-ol (2) (19.6 g, 200 mmol) was added to a mechanically stirred suspension of pyridinium dichromate[8] (112.8 g, 300 mmol) in 400 mL of dry $CH_2Cl_2$. The mixture was stirred for 16 hr at 20°, then 400 mL of ether was added, and the precipitate was filtered. The filtrate was concentrated to approximately 50 mL under reduced pressure, then diluted with 500 mL ether. The resulting mixture was filtered through 2.5 cm of FLORISIL[7a], then concentrated under reduced pressure. Distillation in vacuo yielded 10.79 g (56% yield) of 4.

7a. FLORISIL is a trademark of FLORIDIN CO., U.S.A. for a magnesia silica gel.
8. E. J. Corey and G. Schmidt, *Tetrahedron Letters*, 399 (1979).

Preparation of 1-heptyn-6-ol (5)

A solution of methylmagnesium bromide (114 mmol) was prepared in 12.5 mL dry ether, and cooled to −5°. Aldehyde 4 (7.4 g, 77 mmol) in 20 mL dry ether was added dropwise over 15 min, maintaining the temperature ≦0°. When addition was complete the suspension was stirred at 0° for a further 15 min. Saturated $NH_4Cl$ solution (300 mL) was then added slowly, and the mixture was extracted with ether (4×75 mL). The combined ether extracts were washed with brine, dried ($MgSO_4$), and concentrated in vacuo. Vacuum distillation gave 7.8 g of 5 (91% yield).

Preparation of 6-[(tetrahydro-2H-pyran-2-yl)oxy]-1-heptyne (6)

Alcohol 5 (7.7 g, 68.75 mmol) was dissolved in 75 mL dry ether and cooled to 0°. A few crystals of p-toluenesulphonic acid were added, followed by dropwise addition of 6.35 g (75.6 mmol) of dihydropyran. The solution was warmed to 20°, stirred for 18 hr, and then extracted with saturated aqueous $NaHCO_3$ (25 mL) and brine (25 mL). The solution was dried ($MgSO_4$), concentrated in vacuo, and distilled, yielding 12.96 g of 6 (96% yield).

Preparation of 4-[(tetrahydro-2H-pyran-2-yl)oxy]-1-butyne (7)

3-Butyn-1-ol (3) (7.0 g, 100 mmol) was dissolved in 50 mL dry ether, and the solution was cooled to 0°. A few crystals of p-toluenesulphonic acid were added, followed by dropwise addition of 9.24g (110 mmol) of dihydropyran. The resulting solution was warmed to 20°, stirred for 16 hr, and extracted with saturated aqueous $NaH-CO_3$ (20mL) and brine (20 mL). The solution was dried ($MgSO_4$), concentrated in vacuo, and distilled to give 7 (14.78 g, 96% yield).

Preparation of 5-[(tetrahydro-2H-pyran-2-yl)oxy]-2-pentyn-1-ol (8)

A solution of alkyne 7 (15.4 g, 100 mmol) in dry THF (250 mL) was cooled to −10° under argon, and 48 mL of 2.1M n-BuLi in hexane (202 mmol) was added dropwise, maintaining the temperature below 0°. The solution was stirred for 20 min at 0°, and then powdered dry paraformaldehyde (3.75 g, 125 mmol of $CH_2O$) was added in one portion. The mixture was warmed to 20° over 2 hr, stirred for 16 hr, poured into ice-water (100 mL), and extracted with ether (3×100 mL). The combined ether extracts were washed with brine (50 mL), dried ($MgSO_4$) and concentrated in vacuo. Vacuum distillation yielded a forerun of 2.82 g of alkyne 7, followed by 9.93 g of 8 (66% yield based on recovered starting material).

Preparation of 5-[(tetrahydro-2H-pyran-2-yl)oxy]-2-pentyn-1-yl p-toluenesulphonate (9)

A solution of alcohol 8 (6.16 g, 33.5 mmol) and p-toluenesulphonyl chloride (7.36 g, 38.5 mmol) in dry ether (80 mL) was cooled to −10°. Powdered KOH (25 g, 446 mmol) was added in 5 g portions over 20 min. The resulting suspension was stirred at 0° for 45 min, poured into ice-water (200 mL) and extracted with ether (3×100 mL). The combined ether solutions were washed with brine, dried ($MgSO_4$), and concentrated in vacuo. Final traces of solvent were removed by pumping for 6 hr at 0.1 mmHg, yielding 11.23 g of 9 (99%). This was used without further purification.

Preparation of 3,6-dodecadiyn-1,11-diol (11)

A solution of EtMgBr (38 mmol) in approximately 40 mL dry THF was prepared from ethyl bromide (4.17 g, 38 mmol) and magnesium turnings (2.0 g, 82 mmol), and transferred under argon to a dry flask. Alkyne 6 (6.86 g, 35 mmol) in dry THF (20 mL) was added dropwise over 30 min, during which time the temperature rose to 30° and ethane bubbled off. The solution was stirred at 20°–30° for 2 hr, cooled to 0°, and CuBr (400 mg, 2.8 mmol) was added. The resulting suspension was stirred for 15 min, and tosylate 9 (11.5 g, 34 mmol) in dry THF (20 mL) was added dropwise over 20 min. The mixture was warmed to 20° over 2 hr, stirred for 16 hr, and poured into 100 mL water containing 10 g NH$_4$Cl. The resulting mixture was extracted with ether (3×75 mL), and the combined ether extracts were washed with brine, dried (MgSO$_4$), and concentrated in vacuo to give 12.44 g of yellow oil. About 100 mg were removed for analysis, and a solution of a few crystals of p-toluenesulphonic acid in dry MeOH (75 mL) was added to the remainder. The resulting solution was stirred at 20° for 2 hr, then concentrated in vacuo at 0°. The residue was taken up in ether (100 ML), washed with saturated aqueous NaHCO$_3$ and brine, dried (MgSO$_4$), and concentrated in vacuo. Final purification by flash chromatography[9] (hexanes:EtOAc, 2:3) yielded 4.36 g of 11 (66% yield) as a yellow oil, which rapidly darkened on standing.

Preparation of 11-oxo-3,6-dodecadiynoic acid (12)

Chromium trioxide (12.0 g, 120 mmol) was dissolved in 120 mL of 3.5M H$_2$SO$_4$ (420 mmol) and cooled to −5°. A solution of diol 11 (4.30 g, 22.2 mmol) in acetone (250 mL) was added dropwise over 4 hr. When the addition was complete, the mixture was warmed to 20° over 45 min, then poured into water (400 mL), and extracted with ether (4×150 mL). The combined ether extracts were washed with brine (3×50 mL), dried (MgSO$_4$), and concentrated in vacuo. The crude product was flash chromatographed[9] (hexane:EtOAc:AcOH, 75:75:1), yielding 1.83 g (40% yield) of a highly unstable yellow oil.

9. W. C. Still, M. Kahn and A. Mitra, J. Org. Chem., 43, 2923 (1978).

Preparation of 11-hydroxy-3,6-dodecadiynoic acid (13)

Keto-acid 12 (1.8 g, 8.7 mmol) was dissolved in 25 mL absolute EtOH, and cooled to −20°. NaBH$_4$ (0.456 g, 12 mmol) was added in one portion, and the solution was warmed to 0° over 15 min, then cooled to −20° again. The reaction mixture was then slowly acidified with 3.5N HCl, brine (25 mL) was added, and the solution was extracted with ether (4×25 mL). The combined ether extracts were washed with brine (2×20 mL), dried (MgSO$_4$), and concentrated in vacuo, to give an orange oil, which rapidly darkened in colour. This was used immediately without purification in the next step.

Preparation of (3Z,6Z)-11-hydroxy-3,6-dodecadienoic acid (14)

4 Mmol of P-2 nickel[6] was made by the standard procedure in 30 mL, 95% EtOH. The crude acid 13 was added, and the mixture was stirred under H$_2$ for 5 hr. The solution was then filtered with suction through 5 mm of activated charcoal, rinsing several times with EtOH. The filtrate was concentrated in vacuo at 20°, to an orange-brown oil. Ether (20 mL) was added, and the solution was acidified to pH 3 with 2M HCl. The ether layer was separated, and the aqueous portion was extracted several more times with ether (3×20 mL). The combined ether extracts were washed with brine, dried (MgSO$_4$), and concentrated in vacuo, to yield 1.53 g of crude product. Flash chromatography (hexane:EtOAc:AcOH, 75:75:1) yielded 0.66 g of 13.

6. C. A. Brown and V. K. Ahuja, J. Chem. Soc. Chem. Commun., 553 (1973).

Preparation of (Z,Z)-dodeca-3,6-dien-11-olide (II)

A solution of hydroxy-acid 14 (0.64 g, 3.1 mmol) and dry triethylamine (2.42 g, 24 mmol) in dry acetonitrile (200 mL) was added over 20 hr via a fixed-rate addition funnel and a high dilution head to a refluxing solution of 2-chloro-N-methyl-pyridinium iodide (3.18 g, 12.4 mmol) in dry acetonitrile (200 mL), under argon. The resulting solution was refluxed a further 2 hr, cooled, and concentrated in vacuo. The residue was taken up in pentane (50 mL) and washed with water (50 mL). The aqueous phase was extracted twice more with pentane (25 mL), and the combined pentane extracts were washed with water and brine, dried (MgSO$_4$) and concentrated in vacuo. The residue was flash chromatographed (hexane:EtOAc, 40:1), yielding 45 mg (7.5% yield) of macrolide II.

Scheme I

-continued
Scheme 1

Chemical Synthesis of I

The chemical synthesis of I to be described, also produces a racemic mixture of the enantiomers. The procedure is outlined in Scheme I on the following page. The synthesis of I was also based on the intramolecular esterification of an omega-hydroxy-acid (26). The construction of 26 involves the linkage of three segments: a protected 3-butyn-1-ol, 1,5 dihalopentane and propylene oxide. The addition of HMPA to a mixture of 15 and the lithio salt of 16 resulted in a 62% yield of the chloride (17). Conversion (NaI in acetone) of the chloride to the iodide (18), was required to facilitate the formation of the Grignard reagent. Initiation of Grignard formation for 18 was still difficult despite the use of various reagents (iodine, ethylene dibromide and methyl magnesium bromide) and the application of heat. The addition of ethylbromide to a refluxing mixture of 18 and magnesium in THF was required. Once Grignard formation was complete, coupling to methyloxirane was rapidly effected by the successive addition of cuprous iodide and methyloxirane to an ice-cold mixture[10]. Only a 45.9% yield of the alcohol (19) was obtained despite numerous variations of solvent, temperature and amount of CuI.

10. (a) N. G. Gaylord and E. I. Becker, Chem. Rev., 49, 448 (1951); (b) C. R. Johnson, R. W. Herr and D. M. Weiland, J. Org. Chem., 38, 4263 (1973); (c) B. D. Johnston and K. N. Slessor, Can. J. Chem., 57, 233 (1979).

Diol 20 is obtained in quantitative yield upon removal of the t-butyldimethylsilyl group. The diol 20 was oxidized in acetone to 23 with $CrO_3 \cdot H_2SO_4$ using the inverse addition procedure to minimize formation of ester side products. The keto-acid 23 was purified by crystallization and reduced to give 24 in 67% yield from diol 20. Reduction of the acetylene in 24 to the Z olefin 26 was stereospecific (376:1) with P-2 nickel. Lactonization of 26 was initially attempted using 2,2'-bis-(4-t-butyl-N-isopropyl)imidazolyl disulfide)[11]. Under these conditions no I was observed even when the reaction was refluxed for several hours. The reaction was successfully conducted using 2,2'-dipyridyl disulfide by adding the thioester dropwise to a refluxing xylene solution of silver perchlorate.[12] Using a slightly modified method described herein the enantiomers of I were synthesized.

11. E. J. Corey and D. J. Brunelle, Tet. Lett., 3409 (1976).
12. H. Gerlach and A. Thalmann, Helv. Chim. Acta, 60, 2860 (1977).

Preparation of 1-tert-butyldimethylsiloxy-9-chloro-3-nonyne (17)

To 16 (18.4 g, 100 mmol) in 50 mL of dry THF under nitrogen was added n-butyllithium (66 mL, 1.6M, 105 mmol) over 20 min. After n-butyllithium addition, 23.3 g (100 mmol) of 15 (and 40 mL of dry THF) was added. Dry HMPA (50 mL) was then added dropwise into the mixture resulting in a slightly exothermic reaction. The ice-bath was removed and the reaction was stirred at 23° C. for 30 min. The reaction was diluted with water (250 mL) and extracted with ether (4×75 mL) followed by a brine wash (2×150 mL). The crude product from this reaction, and a second reaction performed under identical conditions (on 165 mmol of 16), were combined and distilled (Vigreux): bp. 95°–112° C. (0.05 mmHg); 47.5 g (62.2% yield). This product was suitable for iodination without further purification.

Preparation of 1-tert-butyldimethylsiloxy-9-iodo-3-nonyne (18)

To 7.9 g (27 mmol) of 17 was added 100 mL of acetone containing 8.2 g (55 mmol) of sodium iodide. The resultant solution was refluxed for 65 hr and then concentrated in vacuo, diluted with water (150 mL) and extracted with ether (3×75 mL). The ether extract was washed with aqueous sodium thiosulfate (2×75 mL) and brine (2×75 mL). Distillation (Vigreux) gave 10.0 g (96% yield) of 18.

Preparation of 1-tert-butyldimethylsiloxy-11-hydroxy-3-dodecyne (19)

To magnesium powder (830 mg, 35 mmol) and 18 (8.7 g, 23 mmol) in 40 mL of dry THF under nitrogen was added ethyl bromide (0.1 mL,=1.3 mmol). Grignard formation was maintained by refluxing for 3 hr. After the iodide (18) was consumed, 2.2 g (11.5 mmol) of cuprous iodide was added. The mixture was cooled in an ice-bath and stirred for 30 min. Propylene oxide (2.7 g, 46 mmol) diluted in 10 mL of dry THF was added dropwise, the reaction stirred for 30 min at 23° C. and then quenched with saturated aqueous ammonium chloride (100 mL). The ether extract (3×75 mL) of the aqueous mixture was washed with brine (3×75 mL). The isolated product was purified by chromatography[9] on 180 g (20 cm×4.5 cm I.D. column) of silica gel (20% EtOAc in hexane) to give 3.3 g (46% yield) of 19.

9. W. C. Still, M. Kahn and A. Mitra, J. Org. Chem., 43, 2923 (1978).

Preparation of 1,11-dihydroxy-3-dodecyne (20)

To a solution of 19 (2.9 g, 9.4 mmol) in THF (15 mL) was added 19 mL of tetra-n-butylammonium fluoride (19 mmole, 1M solution in THF). The reaction was stirred for 1 hr at 23° C. then diluted with 75 mL of water. The aqueous mixture was extracted with ether (3×50 mL) and the ether extract washed with brine (2×50 mL). Product isolation yielded 1.86 g (100%) of the diol (20). No further purification was carried out on 20.

Preparation of 11-hydroxy-3-dodecynoic acid (24)

To a vigorously stirred, ice-cold solution of chromic trioxide (5.4 g, 54 mmol) in 50 mL of 6N sulfuric acid was added dropwise over 3 hr, 1.76 g (8.9 mmol) of 20 in 50 mL of acetone[5]. The reaction was kept in an ice-bath for 30 min and then warmed to 23° C. before workup. Water (200 mL) was added and the reaction extracted with ether (4×75 mL). The ether extract was washed with brine (3×50 mL). Product isolation yielded crude 11-keto-3-dodecynoic acid (23) which was purified by crystallization from 10% ether in hexane (mp 49°–51° C.) to yield 1.28 g (68% yield).

5. B. C. Holland and N. W. Gilman, Syn. Comm., 4, 203 (1974).

To an ice-cold solution of the keto-acid (676 mg, 3.2 mmol) in 20 mL of absolute ethanol was added 244 mg (6.4 mmol) of sodium borohydride. After 5 min the reaction was warmed to 23° C., diluted with cold 5%

HCl (30mL) and extracted with ether. Product isolation gave 680 mg (99% yield) of 24.

Preparation of 11-hydroxy-3Z-dodecenoic acid (26)

To a vigorously stirred mixture of nickel acetate (1 g) and absolute ethanol (25 mL), saturated with hydrogen, was added 5 mL of the filtrate from a solution of sodium borohydride (500 mg) in ethanol (12 mL) and 2N aqueous sodium hydroxide (0.63 mL). After hydrogen evolution had ceased, the black suspension was treated with 0.7 mL of ethylene diamine.[6] Alkyne 24 (643 mg, 3.0 mmol) was added and the reaction stirred for 1 hr at 23° C. The reaction was diluted with brine (100 mL), acidified with 5% HCl and extracted with ether (4×50 mL). The ether extract was washed with brine (2×50 mL). Product isolation gave 620 mg of 26 (96% yield).

[6]. C. A. Brown and V. K. Ahuja, *J. Chem. Soc. Chem. Commun.*, 553 (1973).

Preparation of (Z)-3-dodecen-11-olide (I)

Triphenylphosphine (196 mg, 0.75 mmol) was added to a solution of 2,2'-dipyridyl disulfide (165 mg, 0.75 mmol) and 26 (80 mg, 0.37 mmol) in 4 mL of dry acetonitrile and stirred for 1.5 hr at 23° C. under argon. The yellow solution was then diluted with 26 mL of dry xylenes and added dropwise over 4 hr to a refluxing solution of silver perchlorate (387 mg, 1.9 mmol) in xylenes (50 mL, under nitrogen). The reaction was refluxed for 6 hr after the addition of the thioester, then filtered. The filtrate was diluted with 160 mL of hexane and chromatographed on 80 g (20 cm×3 cm I.D. column) of silica gel in hexane. The column was washed free of xylenes with hexanes (200 mL) and then eluted with 5% EtOAc in hexane to yield lactone I, 61 mg. Kugelrohr distillation of the crude product gave 22 mg (30% yield) of I, bp. 60°-70° C. (0.1 mm).

Preparation of (R)- and (S)-I

Preparation of (R)- and (S)-1-tert-Butyldimethylsiloxy-11-hydroxy-3-dodecyne ((R)-19) and (S)-19)

The Grignard reagent of 18 (4.0 g, 10.5 mmol) was coupled with (S)-propylene oxide[13] (1.2 g, 21 mmol; $[\alpha]_D^{24} -12.8°$, neat), via the procedure described for the preparation of (R,S)-19, to give 1.65 g (42%) of (S)-19 ($[\alpha]_{Obs}^{22} +4.0°$, neat).

[13]. B. Seuring and D. Seebach, *Aelv. Chim. Acta.*, 60, 1175 (1977).

(R)-19 was prepared from 19.0 g (50 mmol) of 18 and 3.5 g (60 mmol) of (R)-propylene oxide[14] ($[\alpha]_D^{24} +13.9°$ (neat)), following the procedure described above. After workup and column chromatography, 4.9 g (31% yield) of (R)-19 was obtained: $[\alpha]_{Obs}^{22} -3.0°$ (neat).

[14]. B. D. Johnston and K. N. Slessor, *Can. J. Chem.*, 57, 233 (1979)

Preparation of (R)- and (S)-11-β-Methoxyethoxymethoxy-3-dodecyn-1-ol ((R)-21) and (S)-(−)-21)

To an ice-cold mixture of (S)-19 (1.2 g, 3.8 mmol) and di-isopropylethylamine (0.74 g, 5.7 mmol) in dry dichloromethane (4 mL), was added 0.71 g (5.7 mmol) of β-methoxyethoxymethyl chloride. After 30 min the reaction was warmed to 23° C. and stirred for 5 hr. The reaction was then diluted with water (15 mL), extracted with dichloromethane (3×25 mL) and washed with brine (2×25 mL). Product isolation yielded 1.60 g of the MEM ether. The MEM ether was stirred for 5 hr in a mixture of AcOH:THF:water (3:1:1, v/v/v) at 23° C. Water (50 mL) was then added to the reaction, and the resultant aqueous mixture was extracted with ether (3×50 mL) and washed with brine (2×50 mL). Chromatography of the isolated product on silica gel (60 g, 15 cm×3 cm I.D. column; 75% EtOAc in hexane) gave 0.78 g (72% yield) of (S)-22. $[\alpha]_{Obs}^{22} +10.8°$.

(R)-22 was prepared from 4.5 g (14.4 mmol) of (R)-19 by the procedure described above except that the tert-butyldimethyl silyl ether was cleaved with tetra-n-butyl ammonium fluoride instead of the AcOH:THF:water mixture. Chromatography yielded 62% (R)-22 from (R)-19, $[\alpha]_{obs}^{22} -10.7°$, (neat).

Preparation of (R)- and (S)-11(-2-Methoxyethoxymethoxy)-3-dodecynoic acid ((R)-25) and (S)-25)

To an ice-cold solution of chromium trioxide (1.1 g, 11 mmol) in 2N sulfuric acid (15 mL) was added dropwise 0.78 g (2.7 mmol) of (S)-22 dissolved in 30 mL of acetone. After the addition was completed (2 hr), the reaction was warmed to 23° C. and stirred for 3 hr. The acetone was removed in vacuo leaving a residue which was diluted with water (50 mL) and extracted with ether (3×50 mL). The ether extract was washed with brine (3×50 mL) and then subjected to product isolation which gave 0.72 g of crude product. This material was utilized for the next step without further purification.

The (R)-enantiomer of 25 was prepared from 2.12 g (7.41 mmol) of (R)-22. To a solution of chromium trioxide (2.97 g, 30 mmol) in 2N sulfuric acid (42 mL) maintained at 10° C., was added (R)-22 (in 85 mL acetone) over 30 min. The reaction was then stirred for 3 hr at 23° C. and worked up by the method described above. Partial purification of the crude product was achieved by chromatography on 170 g (15 cm×5 cm I.D. column) of silica gel (EtOAc:hexane:AcOH, 49.5:49.5:1.0) to give 0.87 g (39% yield) of (R)-25.

Preparation of (R)- and (S)-11-Hydroxy-3-dodecynoic acid ((R)-24) and (S)-24)

To an ice-cold solution of (S)-25 in 35 mL of dry dichloromethane (under nitrogen) was added 13.5 g (60 mmol) of anhydrous zinc bromide (dried under vacuum at 100° C. for 24 hr). The resultant suspension was stirred for 2 hr after which it was filtered, evaporated to dryness and dissolved in ether (50 mL) which was washed with brine (2×50 mL). Chromatography of the crude product on 60 g (15 cm×3 cm I.D. column) of silica gel (EtOAc:hexane:AcOH, 49.5:49.5:1, v/v/v) gave 71.6 mg of (S)-24 (12.5% yield).

A modification of the procedure described above was used for the cleavage of the MEM ether in (R)-25. To a solution of (R)-25 (720 mg, 1.8 mmol) in 20 mL of dry dichloromethane was added 10.7 g (47 mmol) of anhydrous zinc bromide. The suspension was shaken vigorously for exactly 5 min at 23° C., then diluted with 50 mL of brine. The aqueous mixture was acidified (pH 2) with 2N sulfuric acid, extracted with dichloromethane (3×40 mL) and washed with brine (2×50 mL). Product isolation was followed by chromatography on 90 g (23 cm×3 cm I.D. column) of silica gel to yield, 190 mg of (R)-24 (49% yield).

Preparation of (S)-26 and (R)-26

The (S)-enantiomer of 24 (71.6 mg, 0.34 mmol) was hydrogenated in 83% yield with P-2 nickel catalyst by the procedure described for the racemic material.

(R)-26 (153 mg) was prepared in 84% yield by the same procedure.

Preparation of (R)-I and (S)-I

The lactonization of (R)-26 and (S)-26 was carried out by the procedure described for (R,S)-26. Lactonization of 60.3 mg (0.28 mmol) of (S)-26 gave 15.6 mg (28% yield) of (S)-I after chromatography and Kugelrohr distillation, $[\alpha]_D^{22.5} = 70.5°$ (c=0.96, CHCl$_3$).

The lactonization of 128 mg (0.6 mmol) of (R)-26 gave 43 mg (37% yield) of (R)-I after chromatography and distillation, $[\alpha]_D^{22.5} = -78°$ (c=16.4, CHCl$_3$).

Bioassays

All of the bioassays, referred to in this application were conducted utilizing the procedure described in the article by Pierce et al, *Canadian Journal of Zoology*, Volume 59, No. 10, 1981, p. 1980 at 1981.

Figure 2:
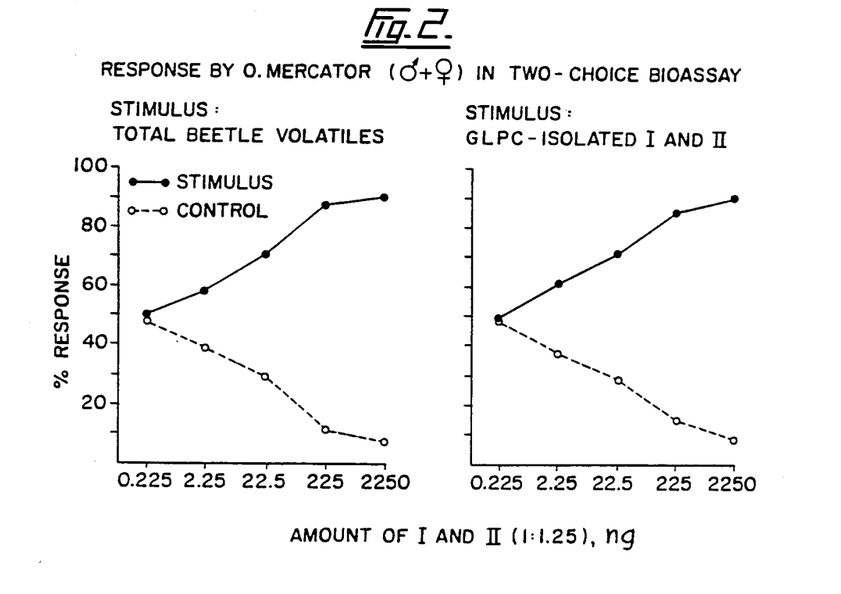
FIG. 2 illustrates the response of *O. mercator* beetles in 2-choice bioassay utilizing both total beetle volatiles and isolated (Z)-12-methyloxacyclododec-4-en-2-one (I), in combination with (Z,Z)-12-methyloxacyclododeca-4,7-dien-2-one (II)

Referring to FIG. 2, it will be seen that similar weights of I and II in a proportion of 1 to 1.25 respectively, will produce similar results as similar weights of the total beetle volatiles, even though each of I and II constitute less than about 30% of the total beetle volatiles obtained in the isolation of them as previously described.

Figure 3:
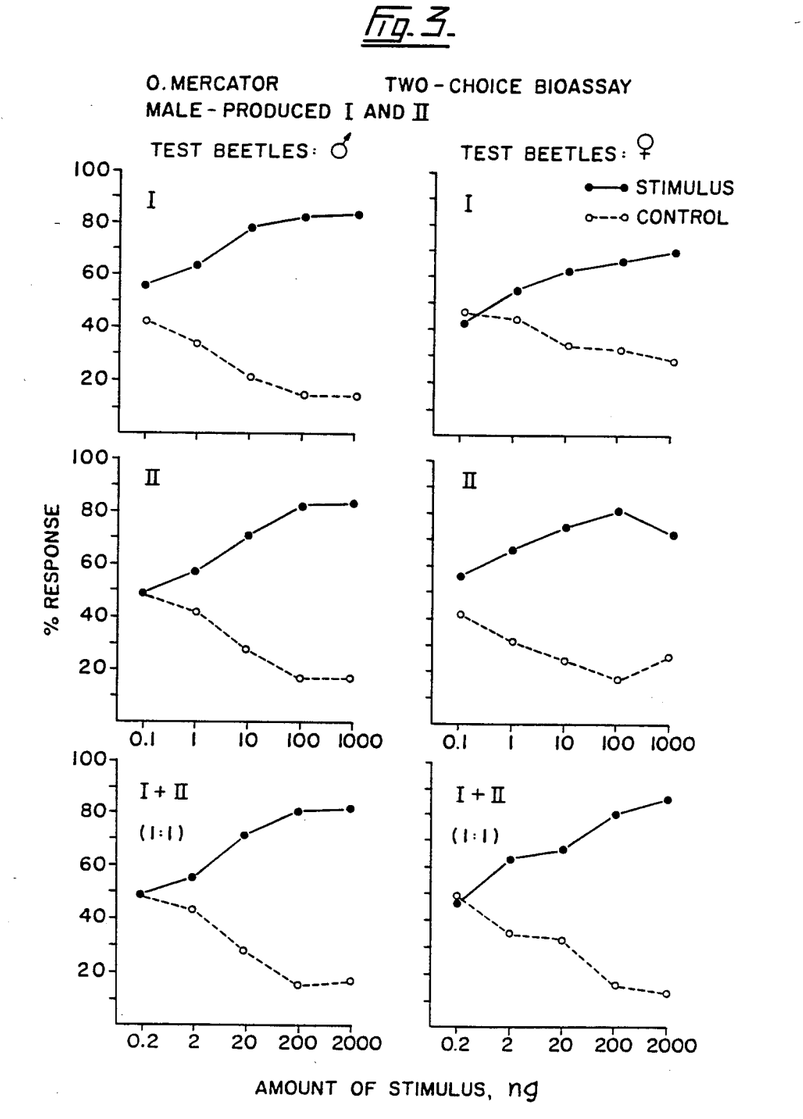
FIG. 3 illustrates the results of a 2-choice bioassay for male and female *O. mercator* beetles separately, utilizing I and/or II.

Referring now to FIG. 3, it will be seen that I appears to be more attractive to male *O. mercator* beetles than female beetles, whereas the reverse appears to be true for II, at least at amounts below 100 ng. Thus, when a trap is to be constructed for use in field conditions, it will generally be preferable to have a mixture of I and II to obtain maximum attraction for both male and female beetles. The foregoing is also illustrated in FIG. 4 wherein an increase of overall response is observed where a mixture of I and II are utilized as the stimulus or attractant.

Figure 4:
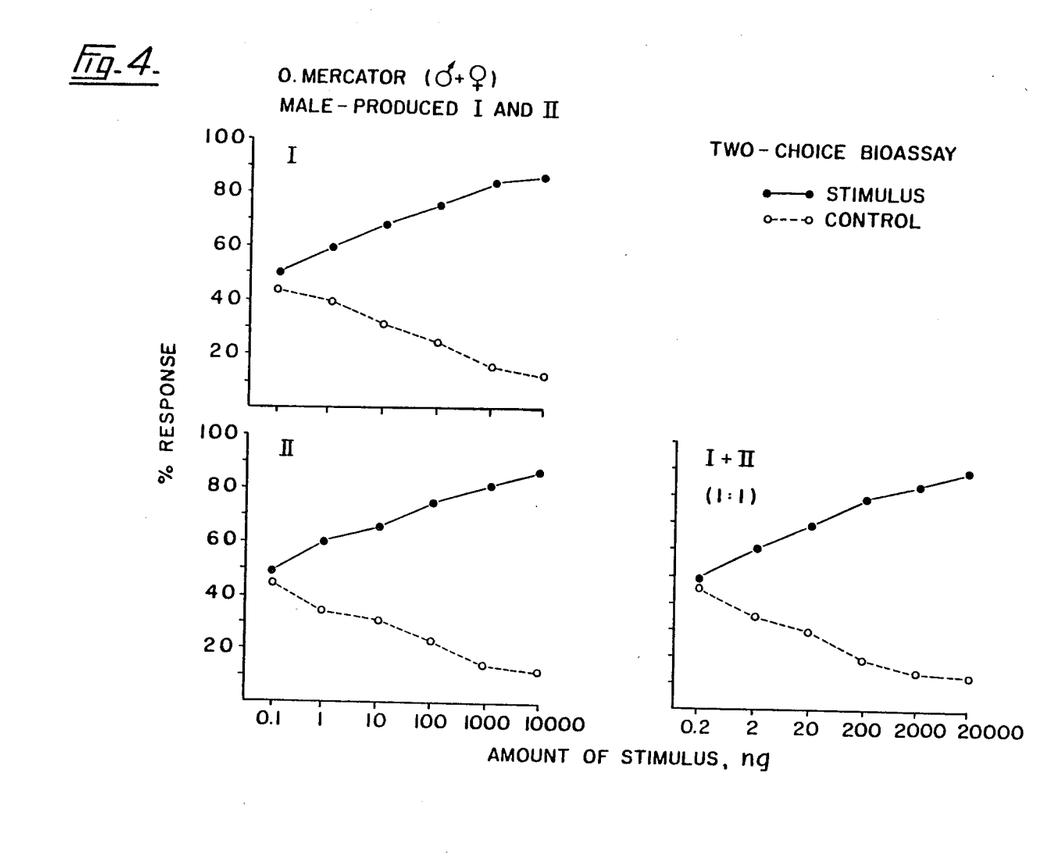
FIG. 4 illustrates the results of a 2-choice bioassay for a mixture of male and female *O. mercator* beetles, utilizing I and/or II.

FIGS. 3 and 4 also illustrate that more than about 5 ng of I or II, separately or together, is required to obtain an effective attraction of the beetles (bearing in mind again that the two-choice bioassay is a comparison of the number of beetles attracted to the test and control trap, that is the percent response equal the number of beetles attracted to the test trap divided by the total, and multiplied by 100).

Figure 5:
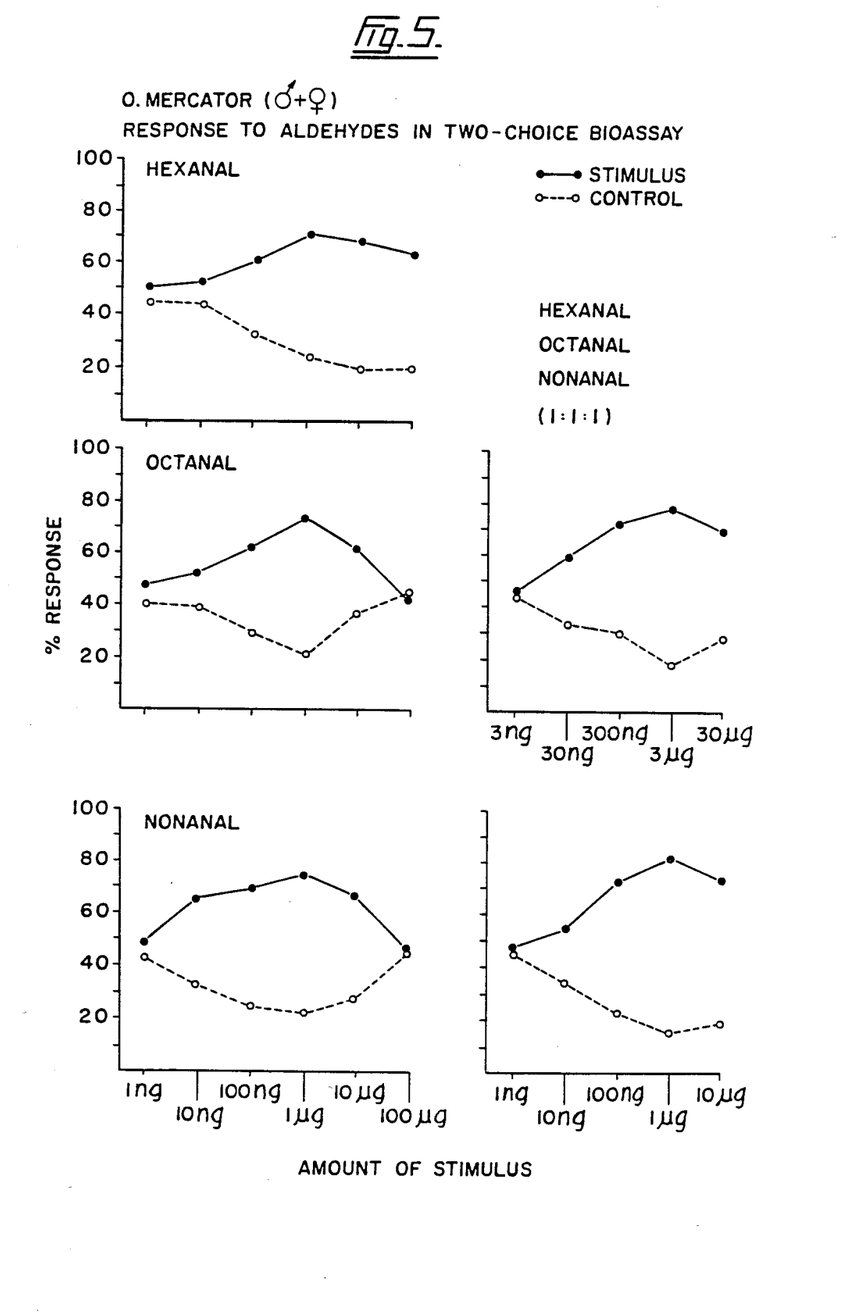
FIG. 5 illustrates the results of a 2-choice bioassay for a mixture of male and female *O. mercator* beetles, utilizing hexanal, octanal, or nonanal, and a combination of the three.

Referring now to FIG. 5, the percentage responses in the two-choice bioassay utilizing the three aldehydes shown, is illustrated in the three graphs on the left-hand side of FIG. 5. The two graphs on the right-hand side of FIG. 5 illustrate the percent response obtained with a mixture of equal weights of hexanal, octanal, and nonanal. There will be noted from FIG. 5 that the response falls off with amounts of aldehyde greater than about 10 ug. However, it is to be borne in mind that the beetles in the bioassay are confined to a small area, and in a trap used in the field, amounts of aldehydes greater than about 10 ug may be satisfactory depending upon the size and construction of the trap, and the area from which it is desired to trap the beetles.

Figure 6:
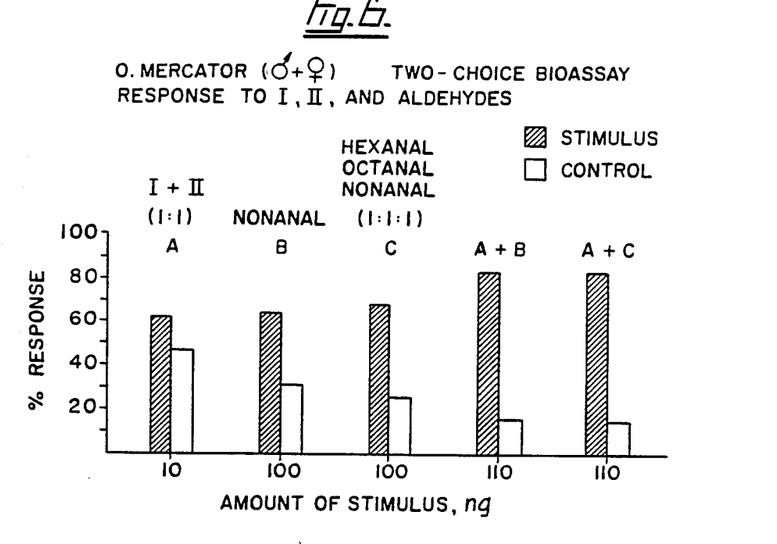
FIG. 6 illustrates the results of a 2-choice bioassay for a mixture of male and female *O. mercator* beetles, utilizing I and II as well as aldehydes separately or in combination with I and II.
Figure 7:
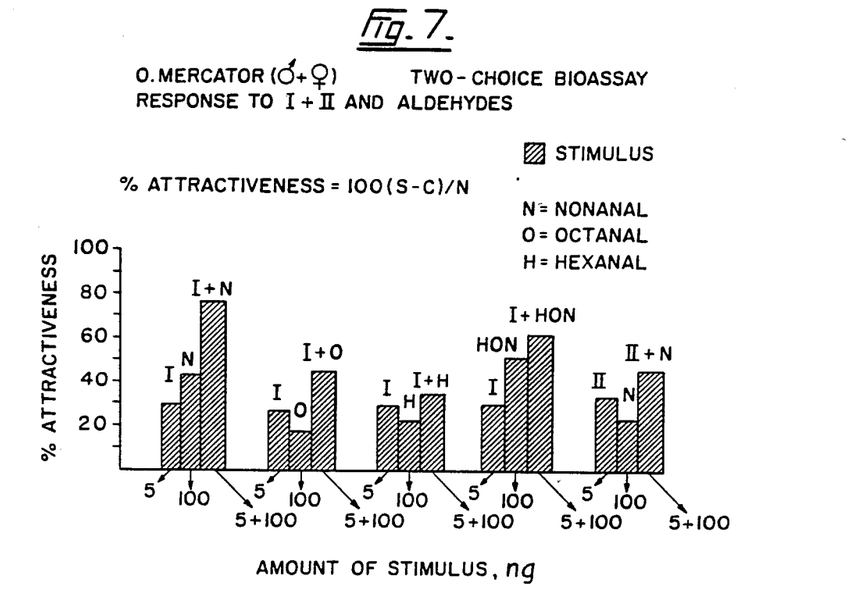
FIG. 7 illustrates the results of a 2-choice bioassay utilizing I or II and aldehydes separately or in combination therewith.

Referring now to FIGS. 6 and 7, FIG. 6 illustrates the bioassay results for the mixture of equal amounts of I and II and for the aldehyde shown, and the foregoing all in combination. In each case, 10 ng of the mixture of I and II was utilized and added to 100 ng of either pure nonanal or a mixture of equal weights of hexanal, octanal and nonanal. It will be seen from FIG. 6 that the mixtures of I and II, in combination with nonanal or a mixture of the three aldehydes, appears to exhibit a synergistic effect with a greater percentage response than is exhibited either from the 10 ng of the I and II mixture, or the 100 ng of nonanal or 100 ng of the hexanal, octanal, nonanal mixture. Such a synergistic effect also appears present in FIG. 7, illustrating the attractiveness (which equals the number in the test trap of the two-choice bioassay minus the number in the control, the difference divided by the total number of beetles and multiplied by 100) of I or II separately and the aldehydes separately, or I or II in combination with various of the three aldehydes or mixtures thereof. Again, a synergistic effect appears to be present in mixing I or II with any of the aldehydes with the greatest effect apparently being exhibited by the mixture of 5 ng of I with 100 ng of nonanal.

All of the above bioassays were conducted utilizing the I or II obtained by the isolation method described above, and not by the chemical synthesis described. It has also been found though that the synthesized (−)-I (i.e. (Z)-(−)-12-methyloxacyclododec-4-en-2-one) is within the limits of experimental uncertainty, apparently as good as an attractant as the I isolated from the beetles. In addition though, as is shown in the following table the R-(−)-I is a more effective attractant in the bioassay than the S-(+)-I.

| Differential Response of *O. Mercator* to Enantiomers of *I* | | | | | | |
|---|---|---|---|---|---|---|
| Stimulus Concentration | (R,S)-*I* | | R-(−)-*I* | | S-(+)-*I* | |
| | S | C | S | C | S | C |
| 0.1 ng | 48.3 | 36.7 | 56.6 | 40.0 | 44.9 | 49.0 |
| 1 ng | 48.3 | 41.7 | 59.7 | 36.1 | 42.4 | 49.3 |
| 10 ng | 54.2 | 37.5 | 66.7 | 22.9 | 50.7 | 45.1 |
| 100 ng | 61.1 | 32.6 | 75.9 | 20.0 | 51.4 | 43.8 |
| 1 ug | 70.8 | 23.3 | 83.3 | 16.0 | 61.6 | 35.6 |
| 5 ug | | | 81.3 | 16.7 | | |

S = stimulus pit
C = control pit

It is also apparent from the above table that S-(+)-I at least does not inhibit the activity of the (−)-I to any measurable extent and appears somewhat attractive particularly at higher amounts. Of course, in any trap utilizing I or II, a racemic mixture of the compound used is particularly convenient since such a racemic mixture will likely be produced by most chemical synthesis routes.

It should also be noted from the above that all of the bioassays indicate an increasing attraction with increased amounts of I or II. In this regard then, at least with the amounts of I and II utilized, there is not any decrease of attraction beyond any particular amount of I or II as is often encountered with other pheremones.

Use of Attractants

Figure 8:
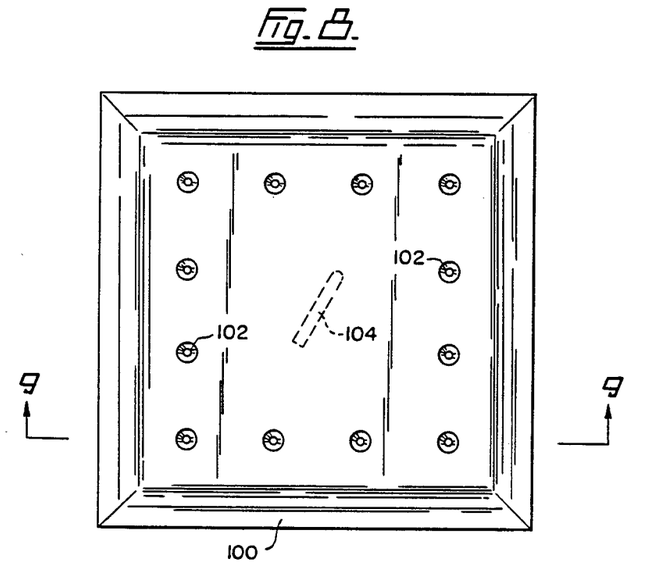
FIG. 8 is a top plan view of a typical sample trap containing the attractants.
Figure 9:
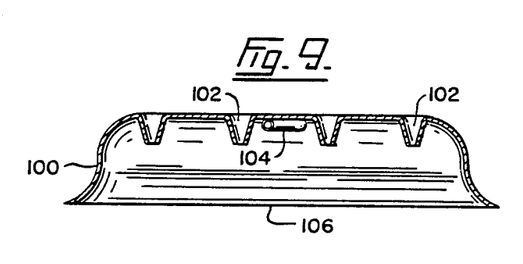
FIG. 9 is a vertical cross section of the trap of FIG. 8.

Referring now to FIGS. 8 and 9 there is shown a typical simple trap in which the above described attractants may be utilized, the trap typically being used to monitor for the presence of *O. mercator*. The trap consist of a dish 100, typically made of plastic, in one end of which is provided a plurality of holes 102 in the form of passages most clearly shown in FIG. 9. The other end of the dish is covered by sticky tape 106, in such a manner that the sticky surface of the tape is exposed upwards when the trap is in the position shown in FIG. 9. A hollow fibre 104 is provided which is sealed at one end and open at the other, and within which is accommodated the attractant chemicals (again either I or II, or hexanal, octanal or nonanal, or mixtures of any of the foregoing). In addition, to avoid loss of the attractant when the trap is stored, a suitable cover (not shown) can be provided for the dish 100 which covers the holes 102. When in use, such a cover is removed so as to expose the trap to beetles, and the trap positioned on a solid surface with the tape 106 on the downward side of the trap. Beetles attracted by the attractant in hollow tube 104 will crawl up the sloping sides of the dish 100 and down through the holes 102, to be trapped inside the trap on tape 106.

It should of course be borne in mind though, that although one particularly simple type of trap has been disclosed, the attractant described can be contained within any of many of well-known suitable traps.

In addition, in constructing any trap containing the attractants as presently described it will be borne in mind that the rate of evaporation of the attractant and hence the effective time period over which the trap will function as well as the range from which O. mercator will be attracted, will depend on factors which can be varied as desired. Such factors include the amount of the attractant, the construction of the fibre in particular, as well as the number and size of holes. As a practical matter though a trap having a practically useful range and lifetime would require about 10 ug of an attractant as described.

As will be apparent to those skilled in the art in light of the foregoing disclosure, many alterations and modifications are possible in the practice of this invention without departing from the spirit or scope thereof. Accordingly, the scope of the invention is to be construed in accordance with the substance defined by the following claims.

We claim:

1. A method of trapping *O. Mercator* beetles comprising exposing a trap in the vicinity of the beetles, which trap contains an amount of an unsaturated oxacyclododecanone sufficient to attract *O. Mercator* beetles, the unsaturated oxacyclododecanone selected from the group consisting of (Z)-12-methyloxacyclododec-4-en-2-one and (Z,Z)-methyloxacyclododeca-4,7-dien-2-one.

2. A method as described in claim 1 comprising exposing the trap in which the attractant comprises at least 10 ug of the unsaturated oxacyclododecanone.

3. A method of trapping *O. Mercator* beetles comprising exposing a trap in the vicinity of the beetles, which trap contains at least 100 ug of a normal alkyl aldehyde selected from the group consisting of hexanal, octanal, and nonanal.

* * * * *